(12) United States Patent  
Morhain et al.

(10) Patent No.: US 8,393,060 B2
(45) Date of Patent: Mar. 12, 2013

(54) QUICK RELEASE BUCKLE WITH VOLATILE SUBSTANCE DIFFUSION MEANS

(75) Inventors: Cedric Morhain, Cerdanyola Del Valles (ES); Fabio Marchetti, Trento (IT)

(73) Assignee: Zobele Espana, S.A. (ES)

( * ) Notice: Subject to any disclaimer, the term of this patent is extended or adjusted under 35 U.S.C. 154(b) by 285 days.

(21) Appl. No.: 12/667,036

(22) PCT Filed: Jun. 25, 2008

(86) PCT No.: PCT/EP2008/058111
§ 371 (c)(1),
(2), (4) Date: Mar. 29, 2010

(87) PCT Pub. No.: WO2009/003900
PCT Pub. Date: Jan. 8, 2009

(65) Prior Publication Data
US 2010/0186198 A1    Jul. 29, 2010

(30) Foreign Application Priority Data
Jun. 29, 2007   (ES) .................................. 200701832

(51) Int. Cl.
*A44B 11/26* (2006.01)
(52) U.S. Cl. ..................... 24/625; 24/573.11; 24/579.09

(58) Field of Classification Search .............. 24/573.11, 24/578.15, 579.11, 614–616, 625, 579.09; 239/34, 36
See application file for complete search history.

(56) References Cited

U.S. PATENT DOCUMENTS

| 5,148,582 | A * | 9/1992 | Dennis, Jr. ..................... 24/625 |
| 6,226,844 | B1 * | 5/2001 | Lerra et al. ..................... 24/625 |
| 6,712,286 | B2 * | 3/2004 | Baxter et al. ..................... 239/36 |
| 6,757,944 | B2 | 7/2004 | Buscart |
| 2002/0062541 | A1 * | 5/2002 | Fildan et al. ................. 24/578.1 |
| 2003/0061831 | A1 | 4/2003 | Tsutsumi |
| 2003/0196302 | A1 | 10/2003 | Buscart |
| 2005/0235469 | A1 | 10/2005 | Anscher |
| 2006/0032937 | A1 | 2/2006 | Caserta |
| 2007/0017074 | A1 | 1/2007 | Pontaoe |

FOREIGN PATENT DOCUMENTS

DE    29718371 U1 *   1/1998
WO    WO 03/052033       6/2003

* cited by examiner

Primary Examiner — James Brittain
(74) Attorney, Agent, or Firm — Fulwider Patton LLP

(57) ABSTRACT

The present invention relates to a quick release buckle of those commonly used for temporarily attaching two belt or band sections, for example of a backpack, sports bag, waist packs, harnesses or leashes for dogs, etc. The object of the invention is to provide said buckle with an additional function such that it can be used for diffusing an insecticide and/or air-freshener substance in the atmosphere, for which a buckle component integrates a diffusion element for diffusing a volatile substance.

13 Claims, 8 Drawing Sheets

QUICK RELEASE BUCKLE WITH VOLATILE SUBSTANCE DIFFUSION MEANS

CROSS-REFERENCE TO RELATED APPLICATIONS

This application is the U.S. National Stage of International Application No. PCT/EP2008/058111, filed Jun. 25, 2008, which claims priority to Spanish Application No. P200701832, filed Jun. 29, 2007.

OBJECT OF THE INVENTION

The present invention relates to a quick release buckle of those commonly used for temporarily attaching two belt or band sections, for example of a backpack, sports bag, waist packs, harnesses or leashes for dogs, etc.

The object of the invention is to provide said buckle with an additional function such that it can be used for diffusing an insecticide and/or air-freshener substance in the atmosphere.

BACKGROUND OF THE INVENTION

Quick release buckles such as those shown in patent documents U.S. Pat. No. 6,757,944 or EP-1,745,712 are widely known.

In addition the diffusion devices for diffusing volatile substances have been designed up until now for their use in a localized environment, generally the user's home or vehicle. However a growing demand for devices with greater mobility which can accompany the user, either human or animal, while moving for the purpose of creating a certain atmosphere in which they are located has been detected.

In this sense several devices achieving such functionality have been developed, however they suffer certain drawbacks. Several have diffusion elements assembled on a belt or collar, such that the belt is an obstacle for diffusing the substance. The diffusion element is an annoyance for the user since it is not integrated in the belt.

In known systems the evaporator device is separated a certain distance from the body of the user, whereby using body heat to favor evaporation was not considered.

DESCRIPTION OF THE INVENTION

The present invention relates to a diffusion element for diffusing a volatile substance integrated in a component intended to form part of a quick release buckle. The component for the buckle houses said diffusion element for diffusing a volatile substance, such that this element can be replaced by another element when the substance has run out.

The invention also relates to a quick release buckle having at least one component such as the one previously mentioned, and a second component couplable to the first in the closure of the buckle.

The access for the entrance and exit of the diffusion element is closed in the closed position of the buckle, whereby the diffusion element is only accessible in the open position of the buckle.

DESCRIPTION OF THE DRAWINGS

To complement the description being made and for the purpose of aiding to better understand the features of the invention according to a preferred practical embodiment thereof, a set of drawings is attached as an integral part of said description, in which the following has been shown with an illustrative and non-limiting character.

PREFERRED EMBODIMENT OF THE INVENTION

Figure 1:
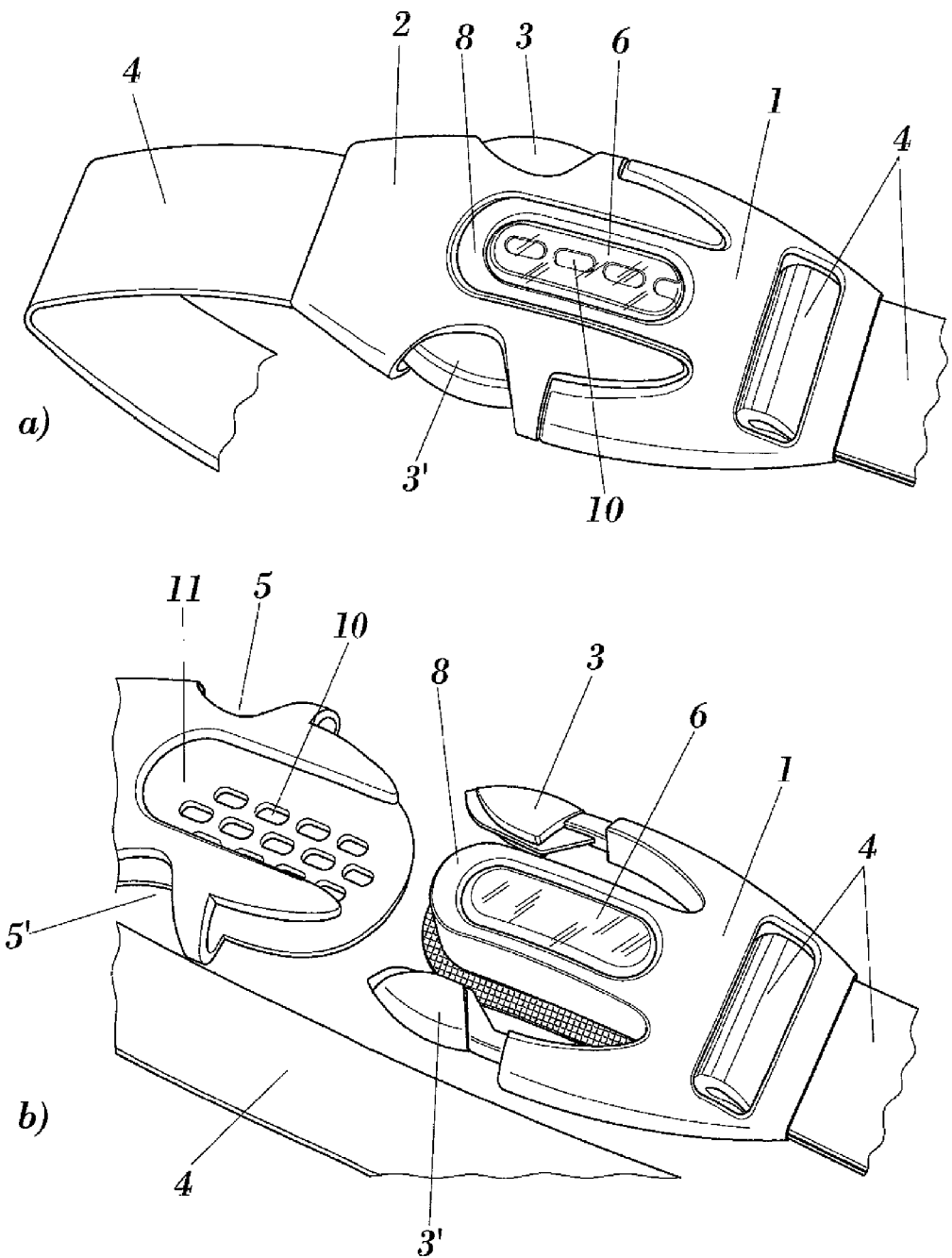
FIG. 1 shows a perspective view of the two components of the buckle object of the invention in a closed position in Figure (a) and in an open position in Figure (b).

FIG. 1 shows the first and second buckle component (1, 2), which are adapted in size and shape for interlocking with one another in a closed position of the buckle in a manner already known in the state of the art. To that end the first component (1) has a U shape and has two flexible side arms (3, 3'). An end of a belt or band (4) can be connected in this first component.

The second component (2) in turn forms a slot able to receive the first component and has side windows in which the ends of the arms (3, 3') are interlocked by snap-fitting.

Based on this conventional structure, the buckle component is characterized in that it removably houses a diffusion element for diffusing a volatile substance, which in this preferred embodiment consists of a container (6) made of transparent plastic material, closed by a vapor-permeable membrane (7). These types of containers are widely known and are described for example in patent application WO 06/042867. The membrane is covered with a sealing sheet which is removed by the user when he or she wishes to begin using the product.

The diffusion element for diffusing a volatile substance can consist of any suitable material, for example a porous material impregnated with a volatile substance.

Figure 2:
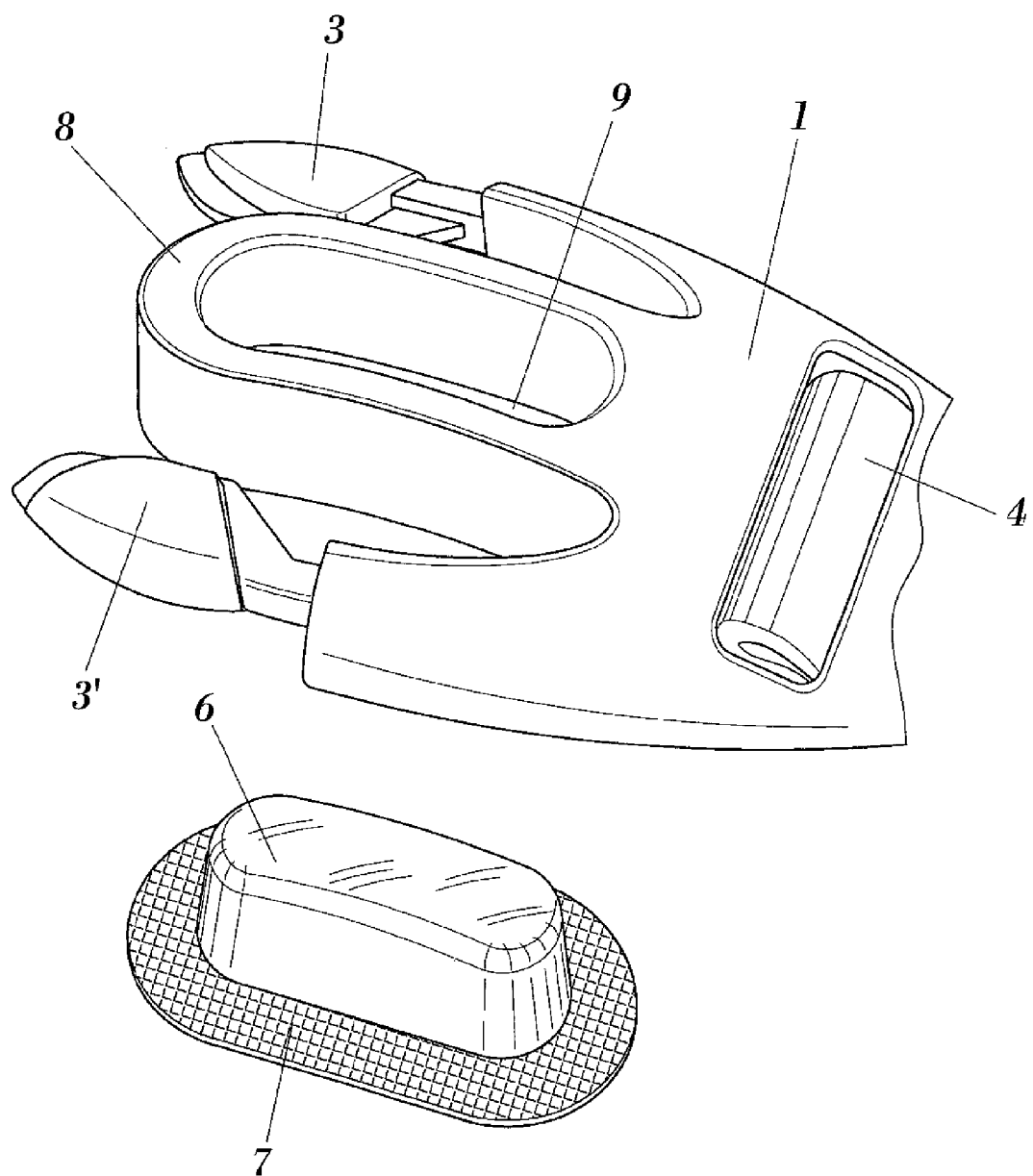
FIG. 2 shows a perspective view of a first buckle component with the diffusion element for diffusing a volatile substance outside the housing.

In the embodiment of FIGS. 1 and 2 the first component (1) has a ring-shaped wall (8) forming an open upper base and an open lower base for housing said container. Said ring-shaped wall (8) is attached to the portion of the component from which the flexible arms start and defines a housing (9) adapted in size and shape for receiving the container (6).

When the first component is not coupled to the second component, i.e., in the open position of the buckle, the container (6) can be inserted in the housing (9) through the opening defining the lower base of the wall (8) as shown in FIG. 2.

However the invention provides that in the closed position of the buckle, i.e., when the first and the second component are coupled, as shown in FIG. 1a, said opening is covered by the second component (2), therefore it is impossible to remove the container (6) while the buckle is closed. This arrangement ensures that the container cannot come out of the buckle during its normal use, and further forms a safety system preventing children or pets from accidentally accessing the volatile substance.

Therefore in order to remove the container, for example when it is necessary to replace it due to having used up the volatile substance, it will be necessary to open the buckle in order to leave the opening accessible and replace the container.

The volatile substance container (6) is transparent and is visible from the outside, therefore the user can see the amount of volatile substance available. Due to its size and arrangement in the center of the buckle, the container does not interfere in the closing and opening operation and it is not necessary to increase the size thereof.

The buckle has at least one orifice in a suitable area in order to allow the exit of the evaporated product, for example towards the body of the user or towards the outside, depending on the type of substance to be evaporated.

In the example of FIG. 1b said at least one orifice (10) is arranged in the second buckle component (2), specifically in a lower base (11) of said component, which is arranged such that in the closed position of the buckle the base (11) is overlapping the membrane (7) of the container, such that the evaporated product exiting the membrane can exit through of the orifices (10). In this case and as can be seen in FIG. 6a, the membrane and the orifices are arranged in the part of the buckle corresponding to the body of the user, which will receive the evaporated product during the use of the buckle. This arrangement can be used for example for diffusing a pest control substance on the body of a pet wearing a harness provided with the buckle object of the invention.

Figure 6:
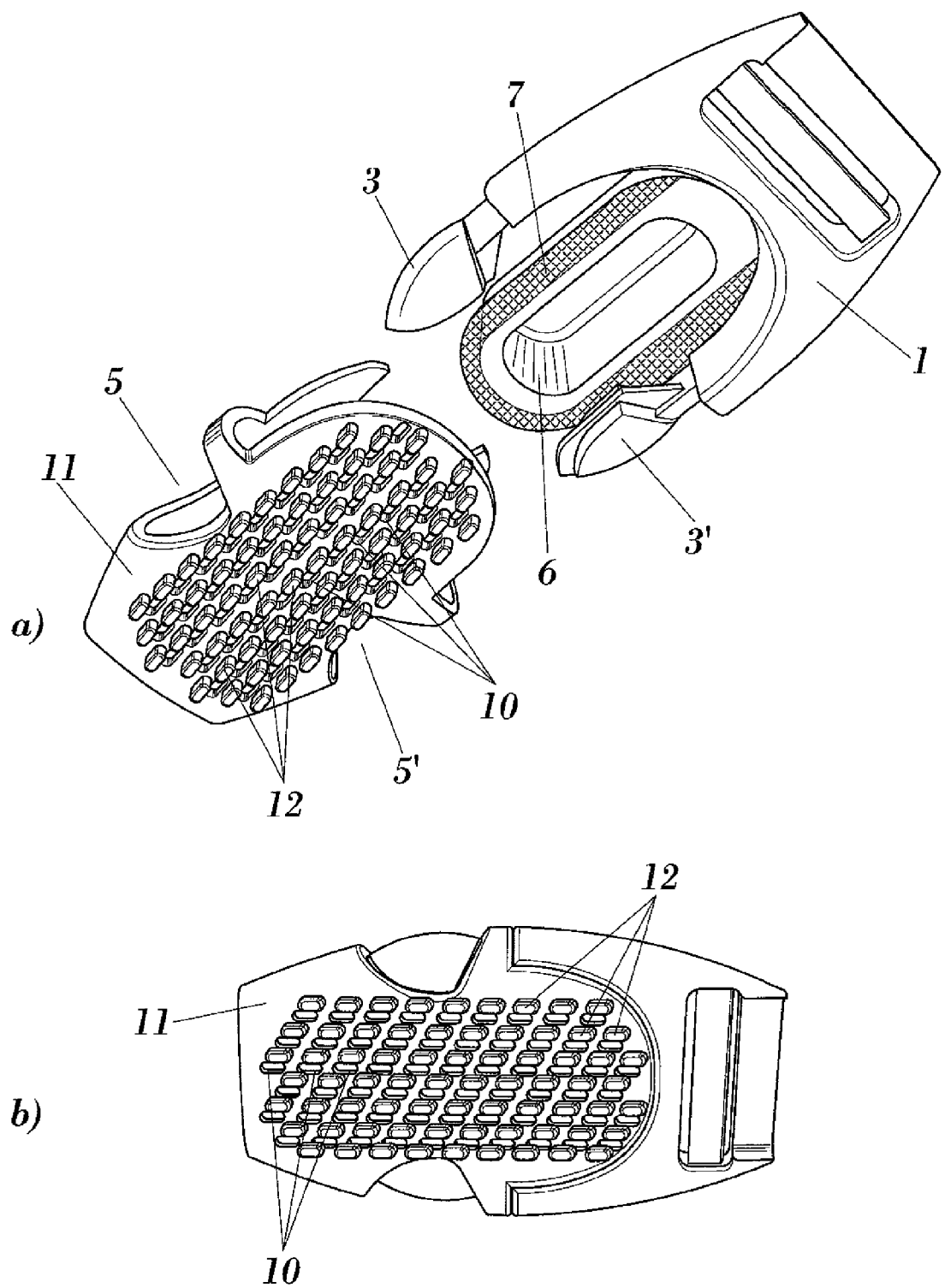
FIG. 6 shows respective perspective and bottom plan views of the two buckle components, uncoupled in Figure (a) and coupled in Figure (b).

As has been especially depicted in FIG. 6, the outer face of the base (11) of the second component (2) is provided with a plurality of protrusions (12), the purpose of which is that of separating the base (11) from the body of the user a suitable distance and therefore allowing the correct diffusion of the evaporated substance without the body of the user blocking the orifices (10).

In other embodiments, the orifices (10) can be arranged in the side or front surfaces of the buckle.

Figure 3:
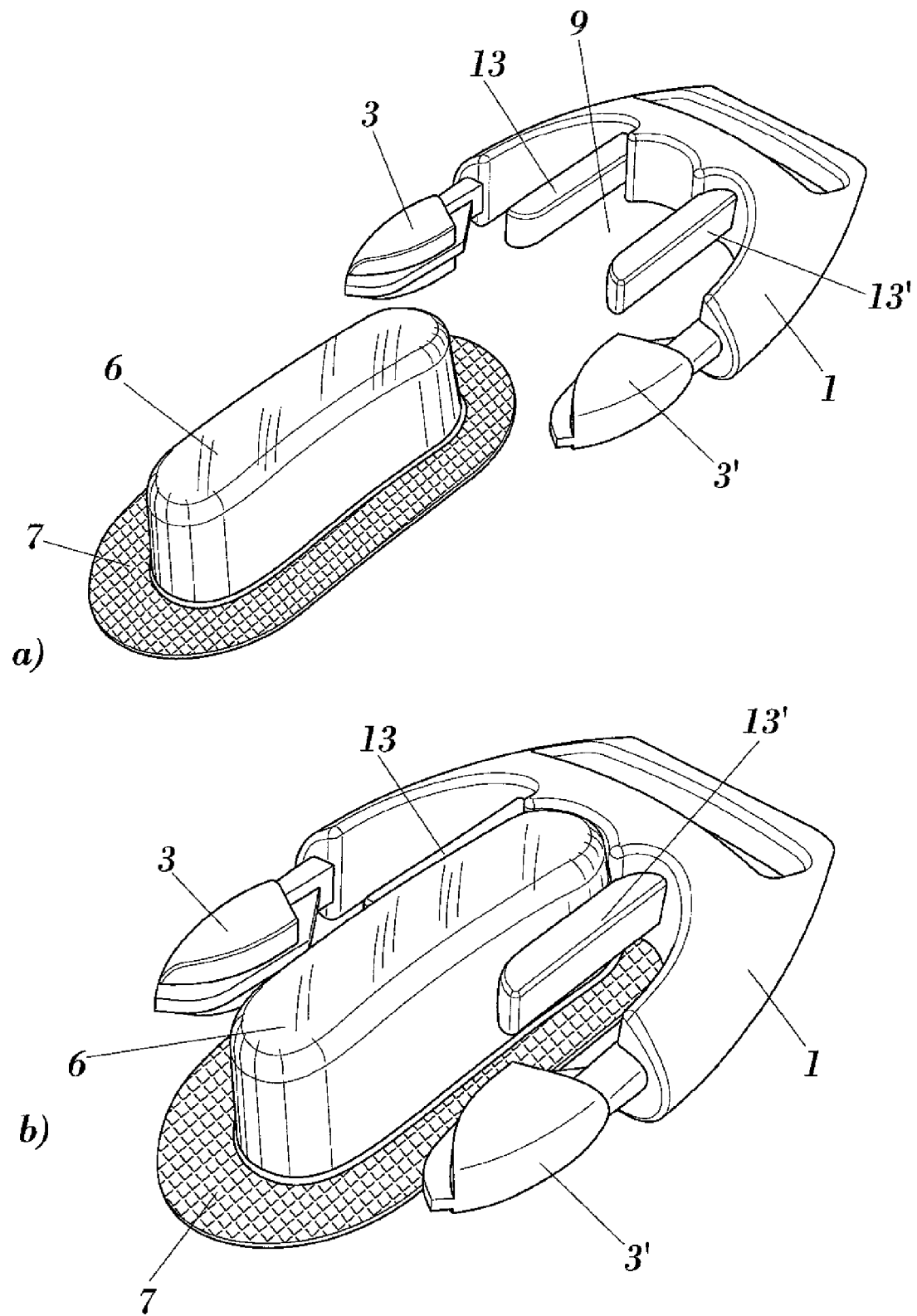
FIG. 3 shows a perspective view of another embodiment of a first buckle component. In Figure (a) the diffusion element for diffusing a volatile substance is outside the housing and in Figure (b) it is inside such housing.
Figure 4:
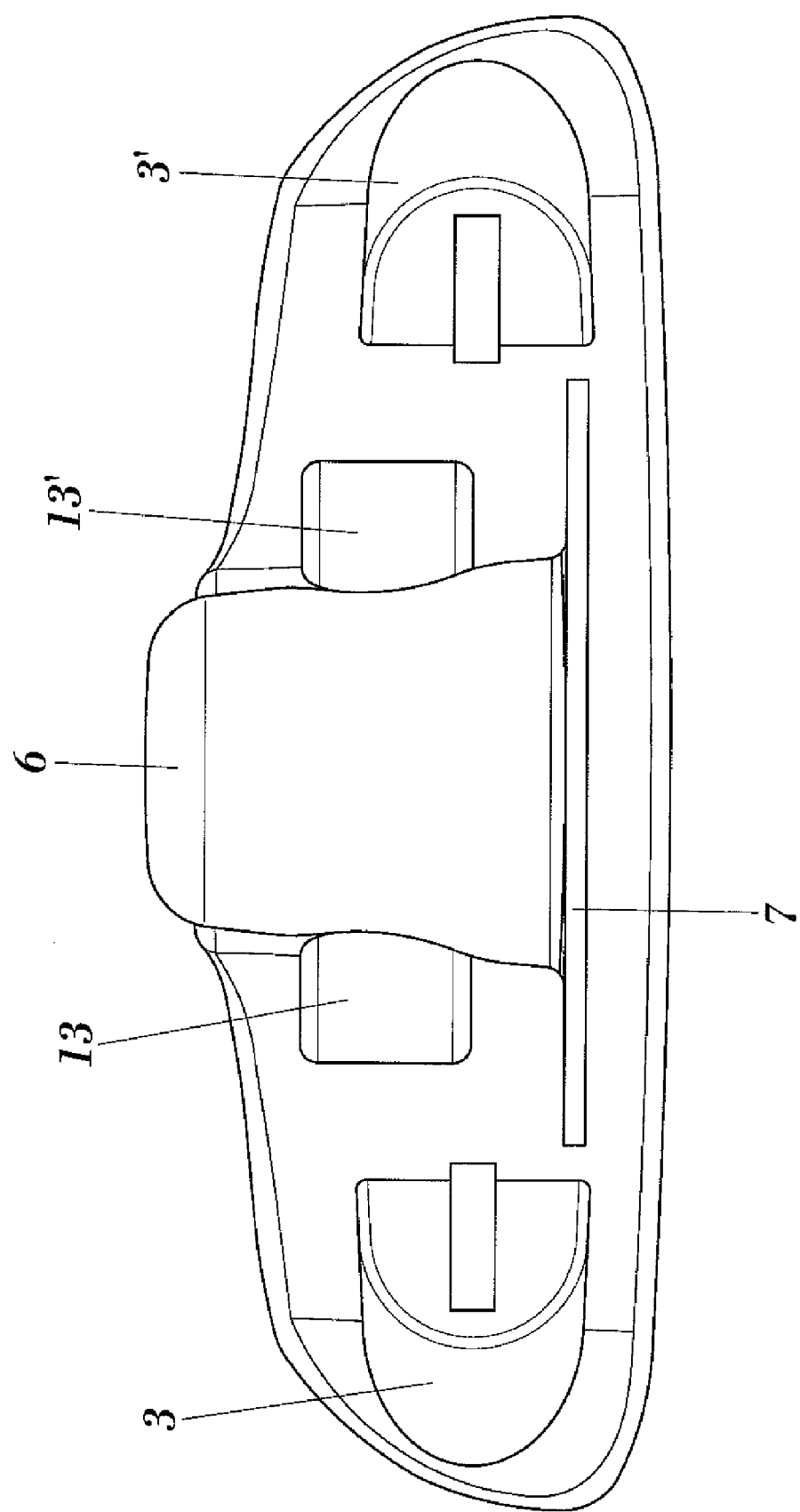
FIG. 4 shows a frontal view of the buckle component of FIG. 3.
Figure 5:
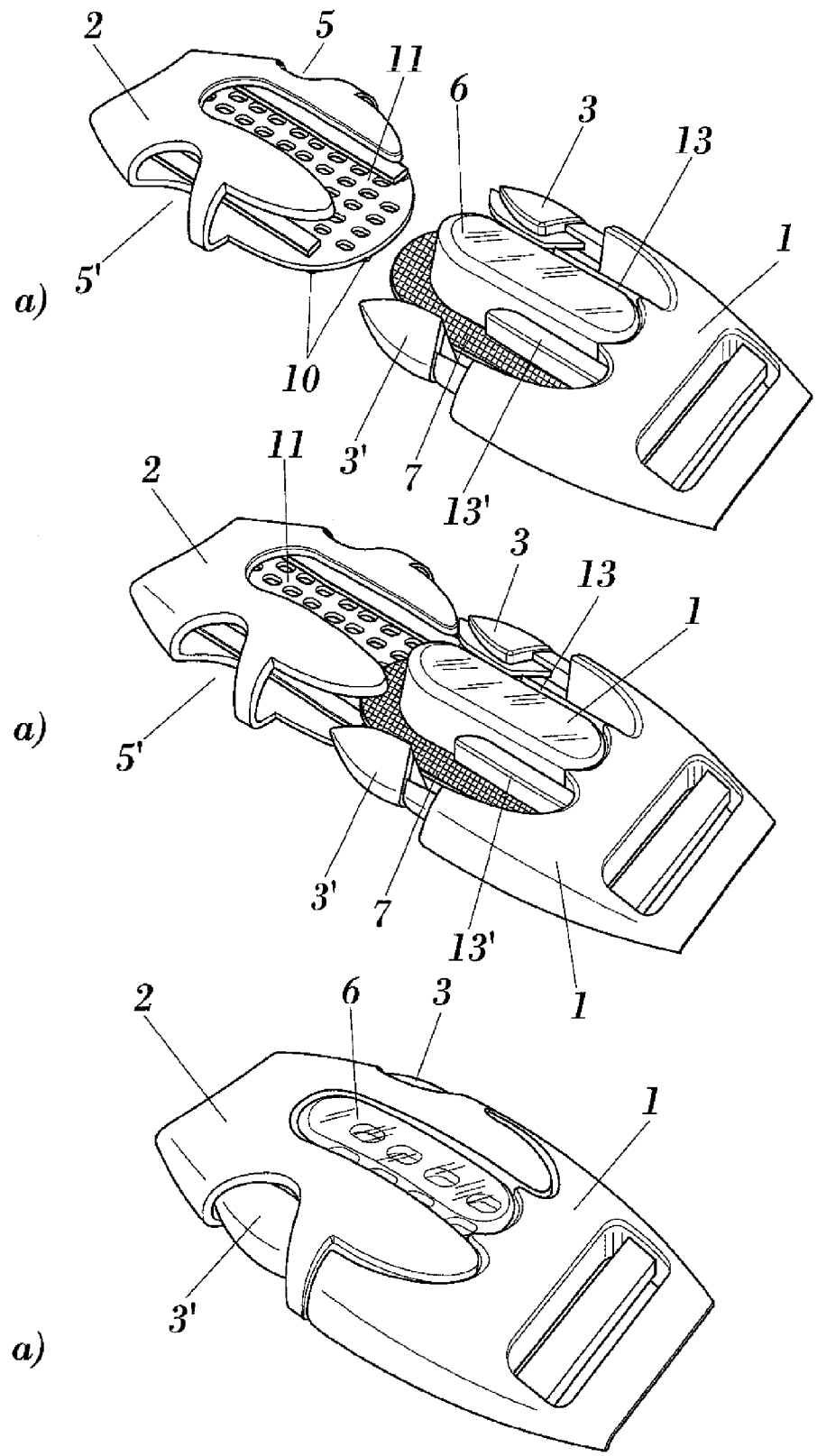
FIG. 5 shows a perspective view of a sequence of three steps during the process of closing the buckle.

In the embodiment of FIG. 3 the housing (9) is defined by a pair of arms (13, 13') parallel to one another and arranged between said side arms (3, 3"). Said arms (13, 13') are attached at one end to the body of the first component whereas the other arms are free, such that the opening or inlet for allowing the entrance of the container (6) is defined between the free ends of said arms (13, 13'). The arrangement of the container between the arms (13, 13') has been depicted in FIG. 4, in which it is shown how the container is pressed between said arms such that it is retained thereby.

Figure 7:
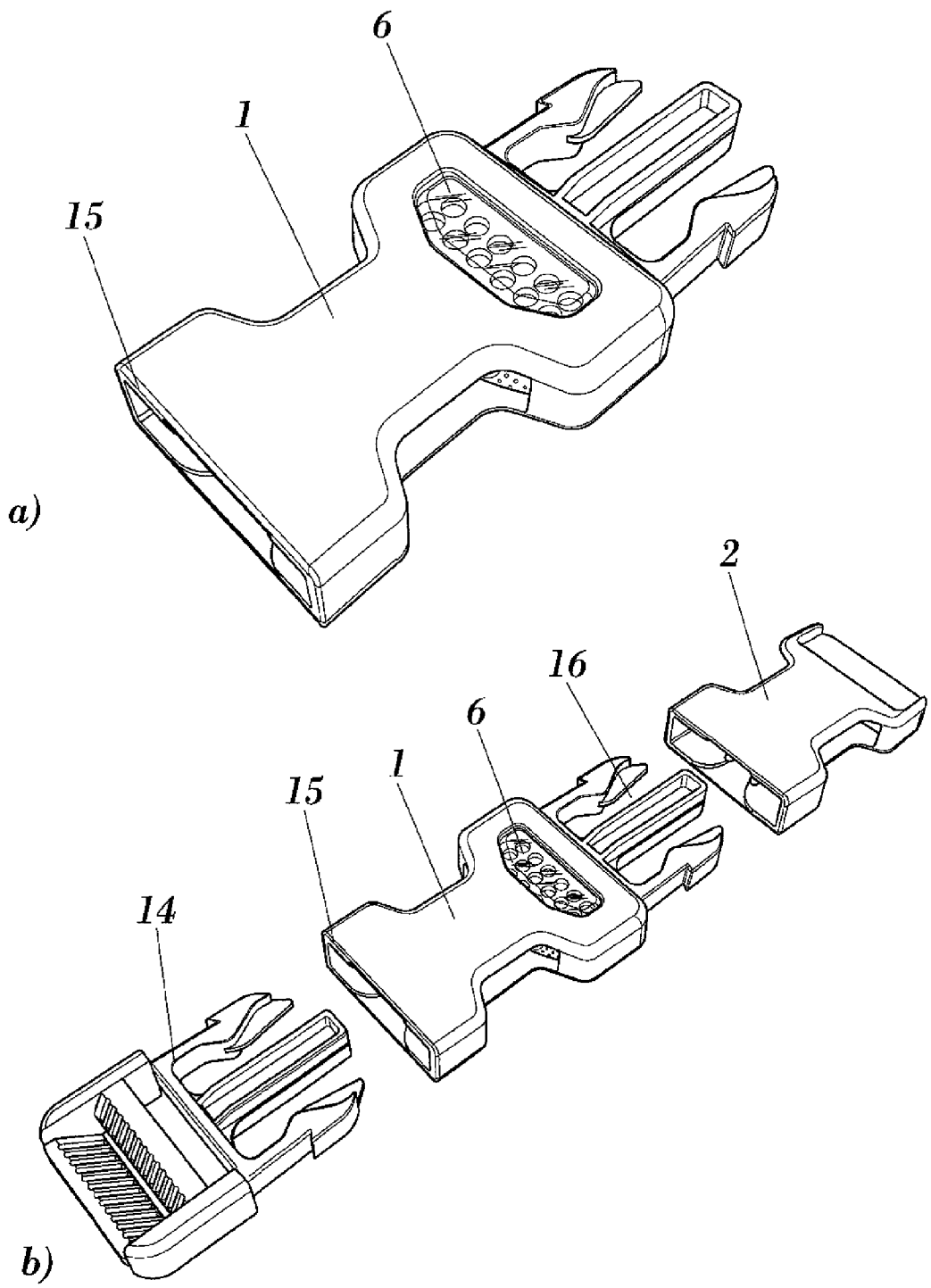
FIG. 7 shows a perspective view of another embodiment of a buckle component according to the invention. Figure (a) depicts the component by itself and Figure (b) depicts the component arranged for being coupled to a conventional buckle.
Figure 8:
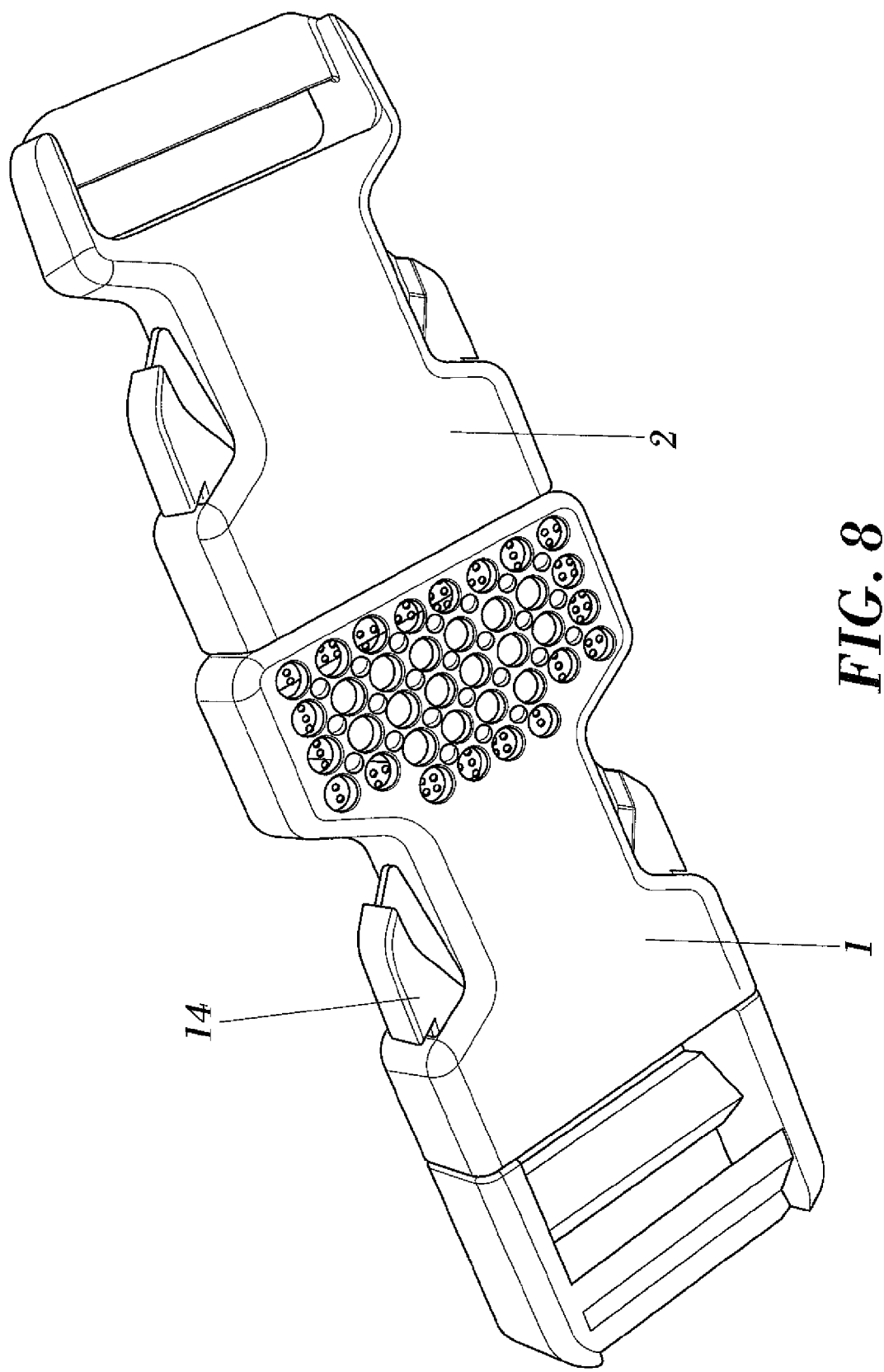
FIG. 8 is a lower perspective view of the component of FIG. 7.

In the embodiment of FIG. 7 the invention consists of a first buckle component (1) housing a diffusion element for diffusing a volatile substance, and which is able to be coupled to the male and female parts of a conventional quick release buckle by itself. With this embodiment, the object of the invention can be applied to already existing buckles without needing to make any modification therein.

The diffusion element has been inserted inside the buckle component during the manufacture of the component, therefore in this case the buckle component is completely disposable since the cartridge with the volatile substance cannot be removed. The diffusion element can logically have another arrangement, for example it could be arranged in the central rib of the part as in the case FIGS. 1 to 3.

In this case the first component (1) has a female end (15) and a male end (16). The female end (15) is adapted to be coupled to the male component of a conventional buckle and the male end (16) in turn is adapted to be coupled to the female component of a conventional buckle.

In other more sophisticated embodiments the buckle can have means for enhancing the evaporation of the product, such as for example a heat accumulator element which has been previously heated, or a heat generator element based on an exothermic catalytic reaction.

Different possibilities of practical embodiments of the invention are described in the attached dependent claims.

In view of this description and set of drawings, a person skilled in the art could understand that the claims of the invention which have been described can be combined in multiple ways within the object of the invention. The invention has been described according to several preferred embodiments thereof, but for a person skilled in the art it will be evident that multiple variations can be introduced in said preferred embodiments without exceeding the object of the claimed invention.

The invention claimed is:

1. A quick release buckle, comprising a first and a second buckle components configured for interlocking with one another in a closed position of the buckle, wherein said first buckle component has a housing and a diffusion element for diffusing a volatile substance, wherein the diffusion element is removably housed within said housing, the housing having an opening for the passage of said diffusion element, characterized in that said first and a second buckle components are configured so that in the closed position of the buckle, the second buckle component closes said opening of the housing in such a manner that extraction of the diffusion element from the first component is prevented.

2. The buckle according to claim 1, characterized in that the diffusion element for diffusing a volatile substance comprises a container closed by a vapor-permeable membrane.

3. The buckle according to claim 1, characterized in that the diffusion element for diffusing a volatile substance comprises a material impregnated with a volatile substance.

4. The buckle according to claim 1, characterized in that the diffusion element for diffusing a volatile substance comprises a porous material.

5. The buckle according to claim 1, characterized in that it has at least one orifice arranged for allowing the exit of an evaporated product towards the outside of the buckle.

6. The buckle according to claim 5, characterized in that said at least one orifice is arranged in the second buckle component.

7. The buckle according to claim 1, characterized in that the first buckle component has a U shape and has two flexible side arms for coupling with the second buckle component, and in that said housing is formed by a ring-shaped wall forming an open upper base and an open lower base.

8. The buckle according to claim 7, characterized in that the second buckle component has a perforated base which in the closed position of the buckle is arranged on said open lower base.

9. The buckle according to claim 8, characterized in that the perforated base incorporates a plurality of protrusions in an outer face of said perforated base.

10. The buckle according to claim 7, characterized in that the diffusion element for diffusing a volatile substance comprises a container closed by a vapor-permeable membrane, the container being located between the flexible arms of the buckle.

11. The buckle according to claim 1, characterized in that the first buckle component has a U shape and has two flexible side arms for coupling with the second buckle component, and in that said housing is formed by two arms substantially parallel to one another and arranged between said side arms.

12. The buckle according to claim 11, characterized in that the diffusion element for diffusing a volatile substance comprises a container closed by a vapor-permeable membrane, the container being pressed by said parallel arms.

13. The buckle according to claim 11, characterized in that the diffusion element for diffusing a volatile substance comprises a container closed by a vapor-permeable membrane, the container being located between the flexible arms of the buckle.

* * * * *